United States Patent [19]

Zeitz

[11] 4,185,086
[45] Jan. 22, 1980

[54] TALC COMPOSITIONS
[75] Inventor: Vernon Zeitz, Springfield, Vt.
[73] Assignee: Johnson & Johnson, New Brunswick, N.J.
[21] Appl. No.: 902,638
[22] Filed: May 4, 1978
[51] Int. Cl.² .................... A61K 7/035; A61K 47/00
[52] U.S. Cl. ...................................... 424/69; 424/357
[58] Field of Search ............................ 424/69, 73, 357

[56] References Cited
U.S. PATENT DOCUMENTS 3,278,383  10/1966  White ...................................... 424/69
3,354,175  11/1967  Fruhstorfer et al. .................. 424/73

FOREIGN PATENT DOCUMENTS 1092726  11/1967  United Kingdom ...................... 424/69

Primary Examiner—Allen J. Robinson
Attorney, Agent, or Firm—Steven P. Berman

[57] ABSTRACT

Talc compositions with improved fragrance stability and other desirable characteristics comprising talc, fragrance and polyethylene glycol having a molecular weight of from 100 to 1500.

4 Claims, No Drawings

TALC COMPOSITIONS

BACKGROUND OF THE INVENTION

The present invention relates to talc powder compositions. More particularly, the present invention relates to talc powder compositions with improved fragrance stability characteristics as well as other desirable attributes.

High grade talcs have for many years been used in the form of powder for application to the skin. The talc in its finely divided powdered form is well suited for this purpose. Finely divided talc has thus found wide application in the cosmetic industry and as a powder for treating tender skins, such as those of infants and children, to prevent chafing or other irritation as would occur from diapers or wet clothing.

Very frequently, for many of the above uses of finely divided talc, it is necessary to add various quantities, usually in minor proportions, of fragrance materials, i.e., perfumes, to impart a desired fragrance to the talc.

It is well known that perfumes are extremely delicate and fleeting. Again, it is common knowledge that some odors that are unpleasant in high concentration are distinctly agreeable when in dilute concentration. Certain definite concentrations of perfumes are therefore necessary in products for their pleasant effect on the olfactory senses. In products intended for long shelf life, it is important that the perfume concentration and component ratio retain essentially the same character on aging so that the aroma of the aged product is just as pleasant as that of the freshly prepared product.

Numerous attempts have been made to improve fragrance retention in talc compositions but few of these attempts have solved the problems in a practical manner. Many of the attempts have resulted in improved fragrance stability but have led to other undesirable characteristics in the compositions.

SUMMARY OF THE INVENTION

It is an object of this invention to provide improved talc compositions.

It is another object of this invention to provide talc compositions with improved fragrance stability.

It is a further object of this invention to provide methods of preparing talc compositions with improved fragrance stability.

Other objects of this invention will be set forth in, or be apparent from, the following detailed description of the invention.

The foregoing objects and other features and advantages of the present invention are achieved by a composition comprising a major amount of talc and a minor amount of polyethylene glycol having a molecular weight of from about 100 to about 1500 as well as a suitable amount of a desired fragrance.

Talc compositions in accordance with the above exhibit excellent fragrance stability without any negative side characteristics. In fact, it has unexpectedly been found that such compositions not only demonstrate good fragrance stability but also exhibit reduced "airborne respirable particle" characteristics. In recent years, there has been some discussion and concern voiced with respect to products which are capable of yielding airborne respirable particles during their use. Although little definitive data has been generated as to the effect, if any, of airborne respirable particles in talc compositions, a reduction of same would still be a desirable characteristic and such has been achieved by the compositions of the present invention.

DESCRIPTION OF PREFERRED EMBODIMENTS

A preferred embodiment of the present invention comprises a talc composition consisting of talc, from about 0.1 to 1.0% of polyethylene glycol and from about 0.01 to 1.0% of perfume.

The talc which is useful in the present invention is any cosmetic grade of talc which conforms to the CTFA specifications. Such talc is essentially a white, odorless, fine powder ground from a naturally occurring rock ore and it typically consists of about 90% hydrated magnesium silicate having a structural formula of $Mg_6[Si_8O_{20}].(OH)_4$, with the remainder consisting of naturally associated minerals such as calcite, chlorite, dolomite, kaolin and magnesite and containing no asbestos minerals.

The polyethylene glycol which is useful in the present invention should have a molecular weight of from about 100 to about 1500, preferably about 200-400 and should be in a fluid form for ease of handling. If a polyethylene glycol of molecular weight greater than 1500 is utilized, it would be in solid form and could lead to processing problems.

The polyethylene glycol is utilized in from about 0.1 to 1.0% by weight of the total composition, preferably from about 0.2 to 0.3%. If less than about 0.1% by weight of the total composition is utilized, stability problems occur; and if greater than about 1% is utilized, stickiness, caking and dispersion problems may occur.

The perfumes which are useful in the present invention are any commercial perfumes which result in the fragrance desired by the formulator of the talc compositions. Commercial perfumes are mixtures of many components and these components all contribute to the particular fragrance which is characteristic of the mixture. For obtaining the desired fragrance, the ratio of components might be changed, some components may be added and some omitted.

Examples of typical perfume components which can be formulated to make up a particular pleasant aroma when used in a body powder product include: lemon oil, musk ketone, ionone, diphenyl oxide, cedarwood-terpeneless; geranyl acetate; ylang ylang oil; cedryl acetate, isoeugenol; cinnamic alcohol, aurantheol, methyl anthranilate; vanillin, oil bergamot, eugenol; oil of cananga; citral; tetrahydro linalool; oil patchouly, methyl isoeugenol; hexylcinnamic aldehyde; resil oilbanum, resin balsam fir; musk aurbrette, resin balsam Peru; oil sandalwood, geraniol; terpenyl acetate, benzyl isoeugenol; oil copaiba; oil nutmeg, rhodinol; diphenyl methane; hydroxycitronellal; methyl benzoate; benzyl propionate; oil palmarose; oil orange, oil geranium; methyl gamma ionone; oil of lavender.

The perfume is utilized in an amount of from about 0.01 to 1.0% by weight of the total composition, preferably from about 0.1 to 0.3%. If greater than about 1.0% by weight of perfume is utilized, the fragrance will usually be too strong initially and may deteriorate quickly; and if less than 0.01% by weight of perfume is utilized, the fragrance will not be discernible.

The compositions of the present invention can be prepared by well-known mixing or blending procedures. The polyethylene glycol and perfume are premixed and then blended into the talc. The resulting talc compositions exhibit excellent fragrance stability, good feel and reduced airborne respirable particle characteristics.

Although applicant does not wish to be bound in any way by the following proposed explanation, it is believed that the unexpected enhanced fragrance stability may possibly be a result of the mixing of the polyethylene glycol and perfume together since they are mutually soluble and one thereby raises the boiling point of the mixture and reduces the volatility of the perfumes thereby slowing down the fragrance loss over a period of time.

Specific embodiments of the talc compositions prepared in accordance with the present invention are illustrated by the following representative examples. It will be understood, however, that the invention is not confined to the specific limitations set forth in the individual examples, but rather to the scope of the appended claims.

EXAMPLE I

A talc composition is prepared as follows: 99 grams of fragrance are premixed with 112.5 grams of polyethylene glycol having a molecular weight of 400 in a suitable beaker and stirred until the solution turns clear. To a Twin Shell Blender manufactured by Patterson-Kelly Company and fitted with an intensifier bar to ease processing is charged 44.7885 kg. of talc and the blender motor is turned on for two minutes at which point the intensifier drive motor is turned on for two minutes. The polyethylene glycol/fragrance solution is then slowly added over a period of four to five minutes and mixing is continued for an additional eight to ten minutes. The resulting perfumed talc composition has the following composition:

|  | % W/W |
|---|---|
| talc | 99.53 |
| perfume | 0.22 |
| polyethylene glycol (M.W. 400) | 0.25 |
|  | 100.00 |

EXAMPLE II

In order to demonstrate that talc powder compositions prepared in accordance with the present invention exhibit improved fragrance stability, the following experiment was carried out.

A talc composition is prepared in accordance with the procedure of Example I and a second talc composition is prepared by the same procedure except that no polyethylene glycol is utilized. These talc compositions, A & B respectively, are placed in containers marked "A" and "B" and placed in aging rooms at regulated temperatures of 4°, 21°, 38° and 49° C. for periods up to 12 months. At prearranged times, samples are removed from aging and tested for fragrance character and intensity in accordance with the "Triangular Difference Test for Odor" as set forth in the ASTM Manual on Sensory Testing Methods, ASTM Special Technical Publication 435, 5th printing, anuary 1976, page 24.

Briefly, this test presents three samples simultaneously to a subject. Two of the samples are the same from a single lot and the third sample is from a different lot. The subject is asked to select the sample which he believes to be different. Ten subjects are utilized with each casting a pair of judgments for a total of 20 judgments per comparison. The number of correct responses is compared with the number that theoretically would result from chance alone and the probability of the occurrence of the observed number calculated. If the probability is low, a difference is deemed established.

When the talc compositions, A & B were subjected to the above test, composition A was judged to be significantly stronger in fragrance intensity without any noticeable alteration in fragrance than composition B. This test demonstrates the improved fragrance stability of the compositions of the present invention.

EXAMPLE III

In order to demonstrate that talc powder compositions prepared in accordance with the present invention demonstrate improved reduced "airborne respirable particle" characteristics, the following experiment was carried out.

A 9 oz. sprinkle top container of powder approximately ½ full is placed in a mechanical clamping device and shaken vertically at a fixed rate to deliver about 1 gram of powder. The shaker is located within a closed test chamber 50 cm.×45 cm.×56 cm. high so that any airborne dust is contained within the chamber and is rapidly dispersed and uniformized by means of a small circulating fan. The airborne dust is sampled near the center of said chamber with a 10 mm. nylon cyclone located 25 cm. from and 4 cm. below the shaker and operating at a flow rate of 1.7 l/min. The cyclone separates out the respirable sized particles and delivers them to a Thermo Systems, Inc., Model No. 3210A quartz crystal mass monitor for weighing and determination of the average concentration of airborne respirable particles, as mg/m$^3$. The average airborne respirable particle concentration for the first two minutes after shaking is measured and recorded.

When the talc compositions, A & B as prepared in Example II, were subjected to the above test, composition A was found to generate a significantly lower concentration of airborne respirable particles.

Various other features and embodiments of the present invention not specifically enumerated will be obvious to those skilled in the art, all of which may be achieved without departing from the spirit and the scope of the invention as defined by the following claims.

What is claimed is:

1. A talc powder composition consisting essentially of from about 0.01 to 1% by weight of the composition of perfume, from about 0.1 to 1% by weight of the composition of polyethylene glycol having a molecular weight of from about 100 to 1500 and the balance talc.

2. The composition of claim 1 wherein the polyethylene glycol has a molecular weight of from about 200 to 400.

3. The composition of claim 1 wherein the polyethylene glycol is present from about 0.2 to 0.3 by weight of the composition.

4. The composition of claim 1 wherein the perfume is present from about 0.1 to 0.3% by weight of the total composition.

\* \* \* \* \*